(12) United States Patent
Sato

(10) Patent No.: US 10,433,551 B2
(45) Date of Patent: Oct. 8, 2019

(54) 3-PYRIDYLOXYPHENYLDIHYDROURACIL COMPOUND AND USE THEREOF

(71) Applicant: Sumitomo Chemical Company, Limited, Tokyo (JP)

(72) Inventor: Yuki Sato, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/328,118

(22) PCT Filed: Aug. 24, 2017

(86) PCT No.: PCT/JP2017/030250
§ 371 (c)(1),
(2) Date: Feb. 25, 2019

(87) PCT Pub. No.: WO2018/038192
PCT Pub. Date: Mar. 1, 2018

(65) Prior Publication Data
US 2019/0183123 A1   Jun. 20, 2019

(30) Foreign Application Priority Data

Aug. 26, 2016 (JP) .................. 2016-165426

(51) Int. Cl.
*A01N 43/50* (2006.01)
*C07D 403/12* (2006.01)
(52) U.S. Cl.
CPC ........... *A01N 43/50* (2013.01); *C07D 403/12* (2013.01)
(58) Field of Classification Search
None
See application file for complete search history.

(56) References Cited

U.S. PATENT DOCUMENTS

| | | | |
|---|---|---|---|
| 5,981,436 A | 11/1999 | Drewes et al. | |
| 6,410,484 B1 * | 6/2002 | Takano | A01N 43/54 504/221 |
| 6,537,948 B1 | 3/2003 | Tohyama et al. | |
| 2004/0138063 A1 | 7/2004 | Mito | |

FOREIGN PATENT DOCUMENTS

| | | |
|---|---|---|
| JP | H10500116 A | 1/1998 |
| JP | 2001316375 A | 11/2001 |
| JP | 2002155061 A | 5/2002 |
| WO | 2002098227 A1 | 12/2002 |
| WO | 2002098228 A1 | 12/2002 |

OTHER PUBLICATIONS

English Translation of International Preliminary Report on Patentability dated Feb. 26, 2019 in International Application No. PCT/JP2017/030250.
English Translation of International Search Report dated Oct. 10, 2017 in International Application No. PCT/JP2017/030250.

* cited by examiner

*Primary Examiner* — Jeffrey S Lundgren
*Assistant Examiner* — Tori Strong
(74) *Attorney, Agent, or Firm* — Panitch Schwarze Belisario & Nadel LLP

(57) ABSTRACT

Provided is a compound represented by formula (1):

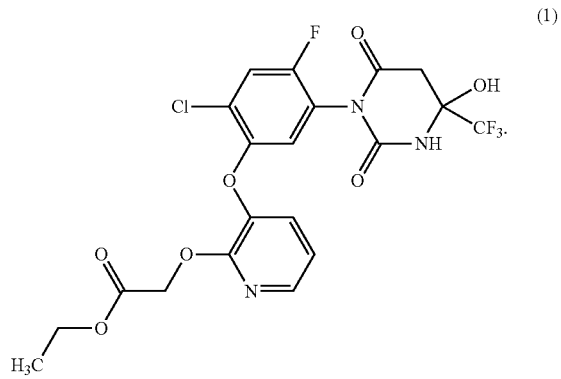

The compound represented by formula (1) has an excellent efficacy for controlling plant diseases, and is thus useful as an active ingredient for an agent for controlling plant diseases.

3 Claims, No Drawings

3-PYRIDYLOXYPHENYLDIHYDROURACIL COMPOUND AND USE THEREOF

CROSS-REFERENCE TO RELATED APPLICATION

This application is a Section 371 of International Application No. PCT/JP2017/030250, filed Aug. 24, 2017, which was published in the Japanese language on Mar. 1, 2018 under International Publication No. WO 2018/038192 A1, which claims priority under 35 U.S.C. §119(b) to Japanese Application No. 2016-165426, filed Aug. 26, 2016, the disclosures of which are incorporated herein by reference.

TECHNICAL FIELD

The present invention is related to a 3-pyridyloxyphenyl-dihydrouracil compound and a use of the same.

BACKGROUND ART

Hitherto, for controlling plant diseases, many compounds have been developed and used practically (see, Non-Patent Literature 1).

CITATION LIST

Non-Patent Document

Non-Patent Document 1: The Pesticide Manual-16th edition, published by British Crop Protection Council (BCPC), ISBN 978-1-901396-86-7

SUMMARY OF THE INVENTION

Problems to be Solved by Invention

An object of the present invention is to provide a compound having an excellent efficacy for controlling plant diseases.

Means to Solve Problems

The present inventor has intensively studied to find out a compound having an excellent control efficacy on plant diseases. As a result, he found out that a compound represented by the following formula (1) has an excellent control efficacy on plant diseases.

That is, the present invention includes the followings.
[1] A compound represented by formula (1):

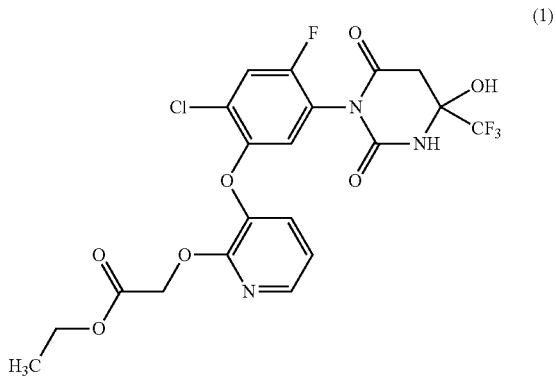 [SMILES: CCOC(=O)COc1ncccc1Oc1cc(N2C(=O)CC(O)(C(F)(F)F)NC2=O)c(F)cc1Cl]

(1)

(hereinafter, referred to as "Compound of the present invention" or "Present compound").
[2] An agent for controlling a plant disease which comprises the compound described in [1] (hereinafter, referred to as "Control agent of the present invention" or "Present control agent").
[3] A method for controlling a plant disease which comprises applying an effective amount of the compound described in [1] to a plant or soil for cultivating the plant.
[4] Use of the compound described in [1] to control a plant disease.

Effect of Invention

According to the invention, plant diseases can be controlled.

Mode for Carrying Out the Invention

The control agent of the present invention is usually prepared by mixing the compound of the present invention with a solid carrier, a liquid carrier, an oil and/or a surfactant and the others, and if necessary, adding other auxiliary agents for formulation such as binders, dispersants and stabilizers and the others, to formulate into wettable powders, water-dispersible granules, flowables, granules, dry flowables, emulsifiable concentrates, aqueous solutions, oils, smoking agents, aerosols, microcapsules, and the others. Such formulations comprise usually 0.1 to 99%, preferably 0.2 to 90% by weight of the present compound.

Examples of the solid carrier include fine powders or granules of clays (for example, kaolin clay, diatomaceous earth, synthetic hydrated silicon oxides, Fubasami clay, bentonite, or acid white clay), talcs, other inorganic minerals (for example, sericite, quartz powders, sulfur powders, active carbon, calcium carbonate or hydrated silica).

Examples of the liquid carrier include water; alcohols (for example, methanol or ethanol); ketones (for example, acetone or methyl ethyl ketone); aromatic hydrocarbons (for example, toluene, xylene, ethyl benzene or methylnaphthalene); aliphatic hydrocarbons (for example, hexane, cyclohexane or kerosene); esters (for example, ethyl acetate or butyl acetate); nitriles (for example, acetonitrile or isobutyronitrile); ethers (for example, diisopropyl ether); amides (for example, dimethylformamide or dimethylacetamide); and sulfoxides (for example, dimethyl sulfoxide).

Examples of the surfactants include alkyl sulfates, alkyl sulfonates, alkyl aryl sulfonates, alkyl aryl ethers, and polyoxyethylenated compounds thereof, polyethylene glycol ethers, polyhydric alcohol esters and sugar alcohol derivatives.

Examples of the other auxiliary agents for formulation include a binder, a dispersant, and a stabilizer. Specific examples include casein, gelatin, polysaccharides (for example, starch, gum arabic, cellulose derivatives or alginic acid), lignin derivatives, bentonite, sugars, water-soluble synthetic polymers (for example, polyvinyl alcohol, polyvinyl pyrrolidone or polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), plant oil, mineral oil, fatty acid and the others.

Examples of the oils and the surfactants that may be mixed with the present compound include Nimbus (registered trademark), Assist (registered trademark), Aureo (registered trademark), Iharol (registered trademark), Silwet L-77 (registered trademark), BreakThru (registered trademark), Sundancell (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7(registered trademark), Emulad (registered trademark), TRITON X 45 (registered trademark), AGRAL 90 (registered trademark), AGROTIN (registered trademark), ARPON (registered trademark), EnSpray N (registered trademark), BANOLE (registered trademark), and the others.

The compound of the present invention may be applied as a control agent of the present invention. Examples of a method for applying the control agent of the present invention is not limited to a specific method as long as the control agent of the present invention can be applied in a substantial applicable form, and include an application to a plant body such as a foliar application, an application to a cultivation area of plant such as a soil treatment, an application to seeds such as a seed disinfection, and the others.

The application rate of the compound of the present invention used in the control method of the present invention may be varied depending on a kind of plant to be applied, a kind and a frequency of occurrence of plant diseases to be controlled, a formulation form, a timing of application, an application method, an application site, a climate condition, and the others. For example, when the compound of the present invention is applied to stems and leaves of plants or soils for cultivating plants, the application rate of the compound of the present invention is within the range of 1 to 500 g per 1,000 m$^2$.

The emulsifiable concentrates, the wettable powders, or flowables etc. are usually applied by diluting them with water, and then spreading them. In this case, the concentration of the compound of the present invention is usually 0.0005 to 2% by weight. The dusts or the granules, etc. are usually applied as itself without diluting them.

The compound of the present invention can be used as an agent for controlling plant diseases in a farmland such as fields, paddy fields, lawns, and orchards.

Examples of the plant diseases which may be controlled by the compound of the present invention include those due to plant pathogens such as filamentous fungi and bacterium, and more specifically include the followings. The descriptions in the below-mentioned parenthesis represent a scientific name of the pathogenic fungi which causes the corresponding plant diseases.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*);

Wheat diseases: powdery mildew (*Blumeriagraminis*), fusarium head blight (*Fusarium graminearum, F. avenaceum, F. culmorum, Microdochium nivale*), yellow rust (*Puccinia striiformis*), black rust (*Puccinia graminis*), brown rust (*Puccinia recondita*), snow mold (*Microdochium nivale, Microdochium majus*), typhula snow blight (*Typhula incarnata, Typhula ishikariensis*), loose smut (*Ustilago tritici*), stinking smut (*Tilletia caries, Tilletia controversa*), eyespot (*Pseudocercosporella herpotrichoides*), glume blotch (*Stagonospora nodorum*), tan spot (*Pyrenophora tritici-repentis*), damping-off caused by rhizoctonia fungus (*Rhizoctonia solani*), and take-all disease (*Gaeumannomyces graminis*);

Barley diseases: powdery mildew (*Blumeria graminis*), fusarium head blight (*Fusarium graminearum, Fusarium avenaceum, Fusarium culmorum, Microdochium nivale*), yellow rust (*Puccinia striiformis*), black rust (*Puccinia graminis*), brown rust (*Puccinia hordei*), dwarf leaf rust (*Puccinia hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia leaf spot disease (*Ramularia collocygni*), and damping-off caused by rhizoctonia fungus (*Rhizoctonia solani*);

Corn diseases: rust (*Puccinia sorghi*), southern rust (*Puccinia polysora*), northern leaf blight (*Setosphaeria turcica*), tropical rust (*Physopella zeae*), southern leaf blight (*Cochliobolus heterostrophus*), anthracnose (*Colletotrichum graminicola*), gray leaf spot (*Cercospora zeae-maydis*), eyespot (*Kabatiella zeae*), phaeosphaeria leaf spot disease (*Phaeosphaeria maydis*), Diplodia (*Stenocarpella maydis, Stenocaipella macrospora*), stalk rot (*Fusarium graminearum, Fusarium verticilioides, Colletotrichum graminicola*), and smut (*Ustilago maydis*);

Cotton diseases: anthracnose (*Colletotrichum gossypii*), grey mildew (*Ramularia areola*), alternaria leaf spot (*Alternaria macrospora, Alternaria gossypii*), and Black root rot caused by Thielaviopsis fungus (*Thielaviopsis basicola*);

Coffee diseases: rust (*Hemileia vastatrix*) and leaf spot (*Cercospora coffeicola*);

Rapeseed diseases: sclerotinia rot (*Sclerotinia sclerotiorum*), gray leaf spot (*Alternaria brassicae*), Phoma stem canker and Phoma leaf spot (*Phoma lingam*);

Sugarcane disease: rust (*Puccinia melanocephela, Puccinia kuehnii*);

Sunflower diseases: rust (*Puccinia helianthi*) and downy mildew (*Plasmopara halstedii*);

Citrus diseases: melanose (*Diaporthe citri*), scab (*Elsinoe fawcetti*), green mold (*Penicillium digitatum, Penicillium italicum*), and Phytophthora disease (*Phytophthora parasitica, Phytophthora citrophthora*);

Apple diseases: blossom blight (*Monilinia mali*), valsa canker (*Valsa ceratosperma*), powdery mildew (*Podosphaera leucotricha*), Alternaria leaf spot (*Alternaria alternata* apple pathotype), scab (*Venturia inaequalis*), anthracnose (*Glomerella cingulata*), blotch (*Diplocarpon mali*), ring rot (*Botryosphaeria berengeriana*), and crown rot (*Phytophthora cactorum*);

Pear diseases: scab (*Venturia nashicola, Venturia pirina*), black spot (*Alternaria alternata* Japanese pear pathotype), and rust (*Gymnosporangium haraeanum*);

Peach diseases: brown rot (*Monilinia fructicola*), scab (*Cladosporium carpophilum*), and Phomopsis rot (*Phomopsis* sp.);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), downy mildew (*Plasmopara viticola*);

Diseases of Japanese persimmon: anthracnose (*Gloeosporium kaki*) and leaf spot (*Cercospora kaki, Mycosphaerella nawae*);

Diseases of gourd family: anthracnose (*Colletotrichum lagenarium*), powdery mildew (*Sphaerotheca fuliginea*), gummy stem blight (*Didymella bryoniae*), corynespora leaf spot (*Corynespora cassiicola*), Fusarium wilt (*Fusarium oxysporum*), downy mildew (*Pseudoperonospora cubensis*), Phytophthora rot (*Phytophthora* sp.), and damping-off (*Pythium* sp.);

Tomato diseases: early blight (*Alternaria solani*), leaf mold (*Cladosporium fulvum*), cercospora leaf mold (*Pseudocercospora fuligena*), late blight (*Phytophthora infestans*) and powdery mildew (*Leveillula taurica*);

Eggplant disease: brown spot (*Phomopsis vexans*) and powdery mildew (*Erysiphe cichoracearum*);

Diseases of brassica family: Alternaria leaf spot (*Alternaria japonica*), white spot (*Cercosporella brassicae*), clubroot (*Plasmodiophora brassicae*), and downy mildew (*Peronospora parasitica*);

Welsh onion disease: rust (*Puccinia allii*);

Soybean diseases: Cercospora leaf blight and purple stain (*Cercospora kikuchii*), Sphaceloma scab (*Elsinoe glycines*), pod and stem blight (*Diaporthe phaseolorum var. sojae*), rust (*Phakopsora pachyrhizi*), target spot (*Corynespora cassiicola*), anthracnose (*Colletotrithum glycines, Colletotrichum truncatum*), Rhizoctonia rot (*Rhizoctonia solani*), septoria brown spot (*Septoria glycines*), frog eye leaf spot (*Cercospora sojina*), stem rot (*Sclerotinia sclerotiorum*), powdery mildew (*Microsphaera diffusa*), phytophthora root and stem rot (*Phytophthora sojae*), downy mildew (*Peronospora manshurica*), and sudden death syndrome (*Fusarium virguliforme*);

Kidney bean diseases: stem rot (*Sclerotinia sclerotiorum*), rust (*Uromyces appendiculatus*), angular leaf spot (*Phaeoisariopsis griseola*), and anthracnose (*Colletotrichum lindemuthianum*);

Peanut diseases: leaf spot (*Cercospora personata*), brown leaf spot (*Cercospora arachidicola*), and southern blight (*Sclerotium rolfsii*);

Garden pea disease: powdery mildew (*Erysiphe pisi*);

Potato diseases: early blight (*Alternaria solani*), late blight (*Phytophthora infestans*), pink rot (*Phytophthora erythroseptica*), powdery scab (*Spongospora subterranea* f. sp. *subterranea*), and Verticillium wilt (*Verticillium alboatrum, Verticillium dahliae, Verticillium nigrescens*);

Strawberry disease: powdery mildew (*Sphaerotheca humuli*);

Tea diseases: net blister blight (*Exobasidium reticulatum*), white scab (*Elsinoe leucospila*), gray blight (*Pestalotiopsis* sp.), and anthracnose (*Colletotrichum theae-sinensis*);

Tabacco diseases: brown spot (*Alternaria longipes*), anthracnose (*Colletotrichum tabacum*), downy mildew (*Peronospora tabacina*), and black shank (*Phytophthora nicotianae*);

Sugar beet diseases: cercospora leaf spot (*Cercospora beticola*), leaf blight (*Thanatephorus cucumeris*), root rot (*Thanatephorus cucumeris*), and aphanomyces root rot (*Aphanomyces cochlioides*), rust (*Uromyces betae*);

Rose diseases: black spot (*Diplocarpon rosae*) and powdery mildew (*Sphaerotheca pannosa*);

Chrysanthemum diseases: leaf blight (*Septoria chrysanthemi-indici*) and white rust (*Puccinia horiana*);

Onion diseases: Botrytis leaf blight (*Botrytis cinerea, B. byssoidea, B. squamosa*), gray-mold neck rot (*Botrytis alli*), and small sclerotial (*Botrytis squamosa*);

Various crops disease: Sclerotinia rot (*Sclerotinia sclerotiorum*);

Japanese radish disease: Alternaria leaf spot (*Alternaria brassicicola*);

Turfgrass diseases: dollar spot (*Sclerotinia homoeocarpa*), and brown patch and large patch (*Rhizoctonia solani*);

Banana disease: Sigatoka disease (*Mycosphaerella fijiensis, Mycosphaerella musicola*); Seed diseases or diseases in the early stages of the growth of various crops caused by fungi from genera of *Aspergillus, Penicillium, Fusarium, Gibberella, Tricoderma, Thielaviopsis, Rhizopus, Mucor, Corticium, Phoma, Rhizoctonia, Diplodia,* and the others;

Viral diseases of various crops mediated by genera of Polymyxa, Olpidium, or the others; and rice damping-off (*Burkholderia plantarii*);

cucumber phytophthora blight (*Phytophthora capsici*), damping-off (*Pythium ultimum*) and cucumber bacterial spot (*Pseudomonas syringae* pv. *Lachrymans*);

eggplant bacterial wilt (*Ralstonia solanacearum*);

citrus canker (*Xanthomonas citri*);

Chinese cabbage slimy soft rot (*Erwinia carotovora*); and the others.

EXAMPLES

Hereinafter, the present invention is explained in more detail by using Preparation example and Test example, however, the present invention should not be limited to these examples.

First, the Preparation example is shown.

Preparation Example (A)

(1)

Six hundred fifty (650) milligrams of the above-mentioned compound represented by formula (A) and 223 mg of potassium cyanate were added to a mixture of 2.6 g of xylene and 1.3 g of acetic acid, and the resulting mixture was stirred at room temperature for 11 hours. Aqueous sodium hydrogen carbonate solution was added to the resulting mixture to adjust the pH of the aqueous layer to 6, and the mixture was extracted with ethyl acetate. The resulting organic layer was washed with saturated saline and concentrated under reduced pressure. The resulting residues were subjected to a silica gel chromatography to give 342 mg of the Present compound.

$^1$H-NMR (CDCl$_3$, 23° C.)δ(ppm): 7.90-7.89 (1H, m), 7.33-7.24 (2H, m), 7.18 (0.4H, br), 7.09 (0.6H, br), 7.01-6.88 (2H, m), 5.75 (0.4H, br), 4.99-4.84 (2H, m), 4.16 (2H, q, J=7.0 Hz), 3.19-3.00 (2H,m), 2.42 (0.6H, br), 1.27 (3H, q, J=7.0 Hz).

ESI-MS (posi): 522 [M+H]$^+$

Next, the test examples are shown.

In the test examples 1 to 4, a non-treated area means an area in which a test was conducted in the same manner as each test example, except that dimethyl sulfoxide was dispensed in place of the present compound diluted with dimethyl sulfoxide.

Test Example 1

Test for Controlling Cucumber Phytophthora Blight Fungi (*Phytophthora Capsici*)

Four point five (4.5) milligrams of the present compound was diluted with 100 μL of dimethyl sulfoxide. One (1) μL portion of the diluted liquid was dispensed into a titer plate (96 wells), and thereto was then dispensed 150 μL of a potato dextrose broth medium (PDB medium) containing zoospores of cucumber phytophthora blight fungi (*Phytophthora capsici*). This plate was cultured at 27° C. for three days, thereby allowing the cucumber phytophthora blight fungi to undergo proliferation, and the absorbance at 600 nm of each well of the titer plate was then measured to determine a degree of growth of the cucumber phytophthora blight fungi. The efficacy was calculated from the determined degree of growth by the below-mentioned "Equation 1". As a result, the efficacy of the Present compound was 90% or more.

$$\text{Efficacy} = 100 \times (X-Y)/X \quad \text{"Equation 1"}$$

where
X: Degree of fungal growth in non-treated area
Y: Degree of fungal growth in treated area Test Example 2

Test for Controlling Damping-Off Fungi (*Pythium Ultimum*)

Four point five (4.5) milligrams of the present compound was diluted with 100 μL of dimethyl sulfoxide. One (1) μL portion of the diluted liquid was dispensed into a titer plate (96 wells), and thereto was then dispensed 150 μL of a Czapek medium containing mycelial suspension of damping-off fungi (*Pythium ultimum*). This plate was cultured at 23° C. for five days, thereby allowing the damping-off fungi to undergo proliferation, and the absorbance at 600 nm of each well of the titer plate was then measured to determine a degree of growth of the damping-off fungi. The efficacy was calculated from the determined degree of growth by the above-mentioned "Equation 1". As a result, the efficacy of the Present compound was 90% or more.

Test Example 3

Test for Controlling Damping-Off Fungi (*Pythium Ultimum*)

One point one two (1.12) milligrams of the present compound was diluted with 100 μL of dimethyl sulfoxide. One (1) μL portion of the diluted liquid was dispensed into a titer plate (96 wells), and thereto was then dispensed 150 μL of a Czapek medium containing mycelial suspension of damping-off fungi (*Pythium ultimum*). This plate was cultured at 23° C. for five days, thereby allowing the damping-off fungi to undergo proliferation, and the absorbance at 600 nm of each well of the titer plate was then measured to determine a degree of growth of the damping-off fungi. The efficacy was calculated from the determined degree of growth by the above-mentioned "Equation 1". As a result, the efficacy of the Present compound was 90% or more.

Test Example 4

Test for Controlling Barley Scald Fungi (*Rhynchosporium Secalis*)

Four point five (4.5) milligrams of the present compound was diluted with 100 μL of dimethyl sulfoxide. One (1) μL portion of the diluted liquid was dispensed into a titer plate (96 wells), and thereto was then dispensed 150 μL, of a potato dextrose broth medium (PDB medium) to which spores of barley scald fungi (*Rhynchosporium secalis*) were inoculated in advance. This plate was cultured at 18° C. for seven days, thereby allowing the barley scald fungi to undergo proliferation, and the absorbance at 600 nm of each well of the titer plate was then measured to determine a degree of growth of the barley scald fungi. The efficacy was calculated from the determined degree of growth by the above-mentioned "Equation 1". As a result, the efficacy of the Present compound was 90% or more.

INDUSTRIAL APPLICABILITY

The compound of the present invention has efficacies for controlling plant diseases, and is useful as an active ingredient for an agent for controlling plant diseases.

The invention claimed is:
1. A compound represented by formula (1):

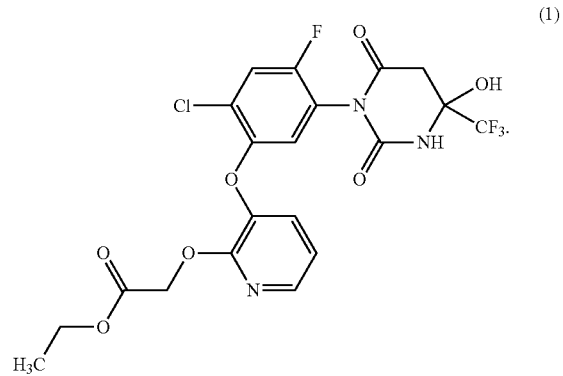 [SMILES: CCOC(=O)COc1ncccc1Oc1cc(N2C(=O)CC(O)(C(F)(F)F)NC2=O)c(F)cc1Cl]

2. An agent for controlling a plant disease which comprises the compound according to claim 1.
3. A method for controlling a plant disease which comprises applying an effective amount of the compound according to claim 1 to a plant or soil for cultivating the plant.

* * * * *